(12) United States Patent
Lieberman et al.

(10) Patent No.: US 12,702,487 B2
(45) Date of Patent: Aug. 11, 2026

(54) SYSTEM AND METHOD FOR AUTOMATED VOLUMETRIC SPINAL ASSESSMENT

(71) Applicant: AGADA Medical LTD., Ramat Hasharon (IL)

(72) Inventors: Isador Lieberman, Plano, TX (US); Samuel Shannon, Karmei Yosef (IL); Jacov Blank, Ramat Hasharon (IL); Damon Eugene Mar, Kansas City, KS (US)

(73) Assignee: AGADA Medical LTD., Ramat Hasharon (IL)

( * ) Notice: Subject to any disclaimer, the term of this patent is extended or adjusted under 35 U.S.C. 154(b) by 0 days.

(21) Appl. No.: 19/193,592

(22) Filed: Apr. 29, 2025

(65) Prior Publication Data

US 2025/0339205 A1 Nov. 6, 2025

Related U.S. Application Data

(60) Provisional application No. 63/642,451, filed on May 3, 2024.

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/0033* (2013.01); *A61B 5/4566* (2013.01); *G16H 10/20* (2018.01);
(Continued)

(58) Field of Classification Search
CPC ..... A61B 34/10; A61B 5/0033; A61B 5/4566; A61B 2034/104; G16H 10/20; G16H 20/40
See application file for complete search history.

(56) References Cited

U.S. PATENT DOCUMENTS 11,803,754 B2 * 10/2023 Pasha ........................ G06T 7/70
12,207,883 B2 1/2025 McKinnon et al.
(Continued)

FOREIGN PATENT DOCUMENTS

CN 113679404 A 11/2021
CN 115736965 A 7/2023
(Continued)

OTHER PUBLICATIONS

Bayard et al., Predicting Spinal Surgery Candidacy From Imaging Data Using Machine Learning, Jul. 2021, 6 page (Year: 2021).*
(Continued)

*Primary Examiner* — Yongjia Pan
(74) *Attorney, Agent, or Firm* — Michele V. Frank; Venable LLP

(57) ABSTRACT

Systems, methods, and computer-readable storage media for measuring spinal canal volume in vertebrates, and more specifically to using Artificial Intelligence (AI) to predict how surgical options will affect spinal canal volume. A system configured as disclosed herein can receive two or more pre-operation medical images capturing at least one functional spinal unit, then calculate an initial spinal canal regional volume using the pre-operation medical images for at least a portion of the at least one functional spinal unit. The system can then calculate, using a neural network, a predicted spinal canal regional volume for at least a portion of the at least one functional spinal unit undergoing various spine surgery options separately, resulting in predicted spinal canal regional volumes corresponding to the plurality of spine surgery options. The system or a surgeon can then select, using that data, one or more of the spine surgery options.

18 Claims, 8 Drawing Sheets

(51) Int. Cl.
*G16H 10/20* (2018.01)
*G16H 20/40* (2018.01)

(52) U.S. Cl.
CPC ........ *G16H 20/40* (2018.01); *A61B 2034/104* (2016.02)

(56) References Cited

U.S. PATENT DOCUMENTS

| | | | | |
|---|---|---|---|---|
| 2014/0187908 | A1 | 7/2014 | Ellermann et al. | |
| 2019/0388099 | A1 | 12/2019 | Zuhars et al. | |
| 2020/0038109 | A1* | 2/2020 | Steinberg | G16H 50/50 |
| 2021/0059822 | A1 | 3/2021 | Casey et al. | |
| 2021/0161682 | A1 | 6/2021 | O'Neil et al. | |
| 2021/0378752 | A1* | 12/2021 | Paul | A61B 34/20 |
| 2022/0000556 | A1* | 1/2022 | Casey | A61F 2/4455 |
| 2022/0013211 | A1 | 1/2022 | Steinberg et al. | |
| 2022/0125602 | A1* | 4/2022 | Zucker | G16H 50/20 |
| 2022/0157459 | A1* | 5/2022 | Siewerdsen | G06N 5/01 |
| 2022/0249168 | A1* | 8/2022 | Besier | A61B 34/10 |
| 2022/0392642 | A1* | 12/2022 | Dasi | G16H 50/50 |
| 2023/0085604 | A1 | 3/2023 | Metcalfe et al. | |
| 2023/0134461 | A1* | 5/2023 | Casey | G16H 50/70 700/97 |
| 2023/0138162 | A1* | 5/2023 | Winston | A61B 34/10 700/98 |
| 2023/0240749 | A1 | 8/2023 | Lev-Tov | |
| 2023/0255696 | A1 | 8/2023 | Roh et al. | |
| 2023/0360768 | A1* | 11/2023 | Shannon | G06N 3/0464 |
| 2024/0065767 | A1* | 2/2024 | Cordonnier | G16H 20/40 |
| 2024/0065800 | A1 | 2/2024 | Frey et al. | |
| 2024/0115324 | A1* | 4/2024 | Mosnier | A61B 34/20 |
| 2024/0156532 | A1* | 5/2024 | Weiman | G06N 5/022 |
| 2024/0374314 | A1 | 11/2024 | Frey et al. | |

FOREIGN PATENT DOCUMENTS

| | | |
|---|---|---|
| CN | 118864498 A | 10/2024 |
| RU | 2396896 | 8/2010 |
| WO | 2016/171570 A1 | 10/2016 |
| WO | 2023/096516 A1 | 6/2023 |

OTHER PUBLICATIONS

International Search Report and Written Opinion mailed Jun. 30, 2025, directed to International Patent Application No. PCT/IB2025/054463; 13 pages.

Liebl, H. et al., (2021). "A computed tomography vertebral segmentation dataset with anatomical variations and multi-vendor scanner data," Scientific Data 8:284, retrieved at <https://doi.org/10.1038/s41597-021-01060-0>; 7 pages.

Ritter, D. et al., (Jan. 2024). "Preoperative 3D Computed Tomography Bone Density Measures Provide Objective Bone Quality Classifications for Stemless Anatomic Total Shoulder Arthroplasty," Journal of Should and Elbow Surgery: vol. 33; No. 7; pp. 1503-1511.

Deshpande, N. et al., (Jan. 2023). "Alternatives to DEXA for the Assessment of Bone Density; A Systematic Review of the Literature and Future Recommendations ," Journal of Neurosurgery: vo., 38; No. 4, pp. 436-445, retrieved at <https://doi.org/10.3171/2022.11.SPINE22875>.

Parr et al., (Dec. 2019). "3D Printed Anatomical (bio)Models in Spine Surgery; Clinical Benefits and Value to Health Care Providers," Journal of Spine Surgery; 5(4); pp. 549-560.

Martín-Noguerol, T. et al., (Jan. 2023). "The Role of Artificial Intelligence in the Assessment of the Spine and Spinal Cord," European Journal of Radiology; retrieved at <https://www.ejradiology.com/article/S0720-048X(23)00040-2/pdf>; 10 pages.

Shi, L. et al., (Apr. 2025). "The Application of Artificial Intelligence in Spine Surgery: A Scoping Review," Journal of the AAOS Global Research & Reviews: vol. 9; No. 4; 13 pages.

Khan, M. et al., (Jan. 2025). "Artificial Intelligence and Its Use in Spinal Surgery and Preparation of Predictive Models: A Systematic Review," Annals of Medicine & Surgery; pp. 171-176.

International Search Report and Written Opinion mailed Dec. 4, 2025, directed to International Patent Application No. PCT/US2025/045338; 14 pages.

* cited by examiner

receiving, at a computer system, at least two pre-operation medical images, the at least two pre-operation medical images each capturing at least one functional spinal unit

704 calculating, via at least one processor of the computer system using the at least two pre-operation medical images, an initial spinal canal regional volume for at least a portion of the at least one functional spinal unit

706

Identifying a plurality of spine surgery options

708 calculating, via the at least one processor executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options

710 selecting, based at least in part on the plurality of predicted spinal canal regional volumes, a selected spine surgery option from the plurality of spine surgery options, such that the selected spine surgery option is executed on the at least one functional spinal unit.

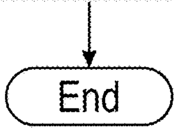

Start 802 receiving, at a computer system, at least two pre-operation medical images, the at least two pre-operation medical images each capturing at least one functional spinal unit 804 calculating, via at least one processor of the computer system using the at least two pre-operation medical images, an initial spinal canal regional volume for at least a portion of the at least one functional spinal unit 806 Identifying a plurality of spine surgery options 808 calculating, via the at least one processor executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options 810 selecting, based at least in part on the plurality of predicted spinal canal regional volumes, a selected spine surgery option from the plurality of spine surgery options, such that the selected spine surgery option is executed on the at least one functional spinal unit.

812 receiving, at the computer system after execution of the selected spine surgery option, at least two post-operation medical images, the at least two post-operation medical images capturing the at least one functional spinal unit 814 updating the neural network based at least in part on the at least two post-operation medical images

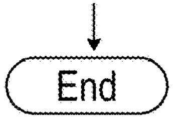

SYSTEM AND METHOD FOR AUTOMATED VOLUMETRIC SPINAL ASSESSMENT

CROSS-REFERENCE

This application claims priority to U.S. provisional patent application 63/642,451, filed May 3, 2024, the contents of which are incorporated herein in their entirety.

BACKGROUND

1. Technical Field

The present disclosure relates to measuring spinal canal volume in vertebrates, and more specifically to using Artificial Intelligence (AI) to predict how surgical options will affect spinal canal volume.

2. Introduction

Spinal stenosis occurs when the spaces within the spinal canal become too narrow. This can put pressure on the spinal cord and nerves that travel through the spine. Doctors and surgeons can recommend procedures (e.g., surgeries) for improving the condition, however accurately predicting the outcomes of possible procedures has been limited.

SUMMARY

Additional features and advantages of the disclosure will be set forth in the description that follows, and in part will be understood from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed are systems, methods, and non-transitory computer-readable storage media which provide a technical solution to the technical problem described. A method for performing the concepts disclosed herein can include: receiving, at a computer system, at least two pre-operation medical images, the at least two pre-operation medical images each capturing at least one functional spinal unit; calculating, via at least one processor of the computer system using the at least two pre-operation medical images, an initial spinal canal regional volume for at least a portion of the at least one functional spinal unit; identifying a plurality of spine surgery options; calculating, via the at least one processor executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

A system configured to perform the concepts disclosed herein can include: receiving at least two pre-operation medical images, the at least two pre-operation medical images each capturing at least one functional spinal unit; calculating, using the at least two pre-operation medical images, an initial spinal canal regional volume for at least a portion of the at least one functional spinal unit; identifying a plurality of spine surgery options; calculating, by executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

A non-transitory computer-readable storage medium configured as disclosed herein can have instructions stored which, when executed by at least one processor, cause the at least one processor to perform operations which include: receiving at least two pre-operation medical images, the at least two pre-operation medical images each capturing at least one functional spinal unit; calculating, using the at least two pre-operation medical images, an initial spinal canal regional volume for at least a portion of the at least one functional spinal unit; identifying a plurality of spine surgery options; calculating, by executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

BRIEF DESCRIPTION OF THE DRAWINGS

FIG. 7 illustrates a first example method embodiment;

FIG. 8 illustrates a second example method embodiment; and

DETAILED DESCRIPTION

Figure 1:
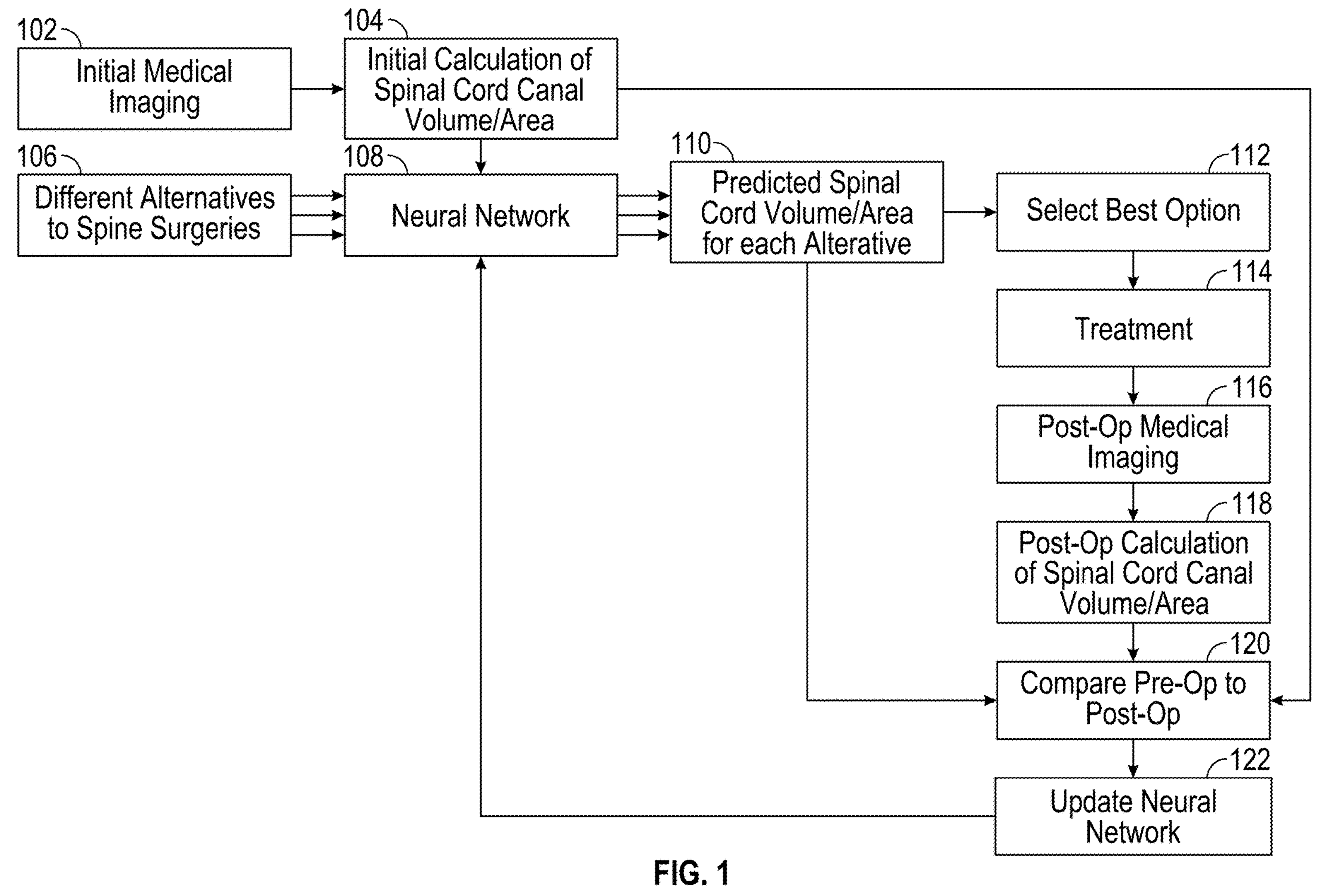
FIG. 1 illustrates an example of a spinal canal stenosis analysis.

Various embodiments of the disclosure are described in detail below. While specific implementations are described, this is done for illustration purposes only. Other components and configurations may be used without parting from the spirit and scope of the disclosure.

As discussed above, spinal stenosis occurs when the spaces within the spinal canal become too narrow. This can put pressure on the spinal cord and nerves that travel through the spine. Those suffering from spinal stenosis often contact doctors or surgeons to help manage or alleviate pain. For example, a laminectomy is a procedure to treat spinal stenosis by removing the bony spurs and bone walls of the vertebrae. Non-limiting examples of laminectomy can include lumbar laminectomy or a cervical laminectomy. In some cases, doctors may perform a discectomy during the laminectomy. In other cases, a laminotomy, where a surgeon removes a portion of the back part of a vertebra (lamina) to thereby create a hole just big enough to relieve pressure in a specific spot, may be a better option. For bones in the neck, laminoplasty may be an option. In yet other cases, tools may be available to remove portions of ligaments at the back of the lumbar spine, thereby reducing pressure in the spinal canal on nerve roots. Determining which option is most likely to increase the spinal canal volume, and thereby relieve the individual of the most pain and restore the best function, has (previous to the system disclosed herein) been difficult to quantify.

Systems configured as disclosed herein can predict the outcome of surgery or other medical procedures in terms of volume, and can correlate the extent of resulting decompression with clinical outcome. First, multiple medical images of the vertebrae in question are taken from multiple angles. Such images capture at least the functional spinal unit in question, with the functional spinal unit including at least the cephalad (toward the head) and caudad (toward the feet) vertebra around the vertebra in question. In some configurations, the images can include the entirety of the spine, or all vertebrae in a spinal region. A functional spinal unit can further include the intervening tissues between vertebra and any discs. The images capturing at least the functional spinal unit can include Computed Tomography (CT), Magnetic Resonance Imaging (MRI), X-ray, and/or other types of medical images. In some configurations, all images may be of a common type (e.g., all CT, all MRI, etc.), whereas in other configurations, the images may be a combination of one or more types of medical images (e.g., one or more CT images with one or more MRI images, etc.). Systems configured as disclosed herein can include any camaras or other imaging equipment necessary to capture the images desired for a given configuration. For example, if the system is configured to utilize CT images, the system may include a CT scanner. Likewise, configurations that require MRIs may include an MRI machine, a configuration that requires an X-ray may include an X-ray machine, etc.

The multiple angles of the medical images allow the system to generate a three-dimensional (3D) model of the vertebrae, spinal process, and spinal canal. This 3D model is a pre-operation, or "pre-op", 3D model. The pre-op 3D model will likely be for a specific sub-portion of the spine, though in some configurations (and if enough images are captured), an entirety of the spine may be represented by the pre-op 3D model. The system then segments the pre-op 3D model into segments vertically (i.e., segments in the transverse plane) and horizontally (i.e., segments in the sagittal and/or coronal planes), allowing for specific locations of the objects within the pre-op 3D model to be identified, and allowing the system to generate volume for specific segments of the spinal canal within the pre-op 3D model. This generated volume may be considered a pre-op volume of the spinal canal. More specifically, this is a pre-op volume of the portion of the spinal canal where spinal stenosis is an issue.

The system can then generate, based on the pre-op 3D model (and the locations of the structures within that model) and the pre-op spinal canal volume (discussed above), a likely post-operation, or "post-op", volume for each different type of medical procedure available. In some cases, the doctor or surgeon can select which medical procedures are evaluated by the system before the post-op volume is generated, whereas in other cases, the system has the medical procedures pre-defined.

To make the post-op prediction, the system can use Artificial Intelligence (AI), such as (but not limited to) a neural network, computer vision, or other software capable of making a weighted, multi-layered correlation that can change/be updated over time. Here, the AI is trained using previous procedures and their respective outcomes. Data used for training can be from past cases, where the outcome is already known. Preferably, before being used for training, the data is cleaned/scrubbed of any information which could lead to identification of the patients involved, thereby complying with privacy considerations. Non-limiting examples of previous procedures can include direct decompression (e.g., laminotomy, foraminotomy, laminectomy, etc.) by removing the bone and soft tissue causing the stenosis, or by indirect decompression (e.g., interbody fusion, distraction instrumentation, using pedicle screws to distract, etc.) by realigning the spine to restore the collapsed disc height and enlarge the foraminal volume. Non-limiting examples of training data can include, for a given procedure: the pre-op 3D model for that procedure, the type of procedure, the volume of the spinal canal within the pre-op 3D model, and/or any other data about the patient (e.g., age, weight, sex, objective/functional gait analysis, measured walking tolerance, subjective data including patient reported outcome measures (e.g., subjective pain level (e.g., "My pain level is [a user provided number]") or walking tolerance (e.g., "Pain becomes unbearable after five minutes of walking")), etc.). Using that training data, the AI can predict, for a current patient, how each possible procedure is likely to affect the spinal canal volume. Based on those results, the system can rank the procedures and display the predicted post-op volumes for each procedure for review by the doctor. In some cases, the training of the AI/neural network can be a multi-stage process. For example, the system may upload all of the data into a deep learning training system, then the system can create clusters of related data on which individual stages are trained. Each subsequent training stage adds a refined layer of outcome prediction to the final AI algorithm.

In some cases, the selected spine surgery option is selected, at least in part, based on which of the plurality of spine surgery options is most likely to reduce stenosis symptoms to the necessary level. For example, a given patient may have nerve pain in their legs resulting from spinal stenosis. While there may be surgeries that could increase the patient's spinal canal volume by 100%, those surgeries may not be necessary for the patient's symptoms to be fully mitigated. Instead, there may be a surgery option which will only increase the patient's canal volume by only 50%, but which fully cures the patient's symptoms. Additional factors, such as, e.g., the patient's age, the level of intrusion/difficulty of the surgery, the patient's ability to recover from the surgery, etc., may also be used by the system in ranking and determining the available procedures.

After a procedure has taken place, additional medical images can be taken, and a post-op 3D model of the vertebrae can be generated. This new, post-op 3D model can be used to generate a post-op spinal canal volume, which can be compared against the predicted post-op volume for that procedure which was previously generated, as well as against the pre-op volume. This comparison data, as well as data about the procedure (e.g., type of procedure, data about the patient, pre-op spinal canal volume, etc.), can then be used as updated training data for the AI system. The AI system can be updated after each procedure, or can be updated after a predetermined amount of time or a predetermined number of procedures have occurred.

In this manner, the system disclosed herein (1) improves accuracy in measuring the spinal canal volume for both pre-op and post op patients experiencing spinal stenosis; (2) identifies the best medical procedure (in terms of volumetric increases and/or patients' symptom relief) available for a given patient; and (3) improves, over time, the post-op predictions.

In some configurations, the system can not only determine the most appropriate surgical solution, but also direct robotic systems to resolve symptoms within patients based on the best identified medical procedure. Such system can be under the direction of a doctor, surgeon, or other medical professional.

FIG. 1 illustrates an example of a spinal canal stenosis analysis. As illustrated, the system first uses initial medical imaging 102 to perform an initial calculation of spinal canal volume/area 104. As discussed above, this can include the generation of a 3D pre-op model of the spinal canal (or a portion thereof). The system has a list or database of different alternatives to spine surgeries 106. In some configurations, types of spine surgeries can be included in the system as possible medical procedures within the different alternatives to spine surgeries 106. The various alternatives 106 and the initial calculation of spinal canal volume/area 104 are input into a neural network 108, or other form of AI, which outputs predicted spinal canal volume/area for each alternative 110. Unlike previous solutions, which may rely solely on a given cross-sectional area, the volume calculations disclosed herein can provide a much clearer prediction regarding possible pinch points within the spinal canal. The doctor or surgeon can then select the best option 112 (preferably in consultation with the patient), and the doctor/surgeon can then perform the treatment 114.

Post-op medical imaging 116 can then occur, followed by a post-op calculation of spinal canal volume/area 118. As discussed above, this can include the generation of a 3D post-op model of the spinal canal (or a portion thereof). This post-op calculation 118 can be compared 120 against the predicted spinal canal volume/area 110 and/or the initial calculation of the spinal canal volume/area 104. Based on this comparison 120, the system can update the neural network 122, adding additional data about the procedure to the training data, then retraining the neural network 108 based on the aggregated data.

Figure 2:
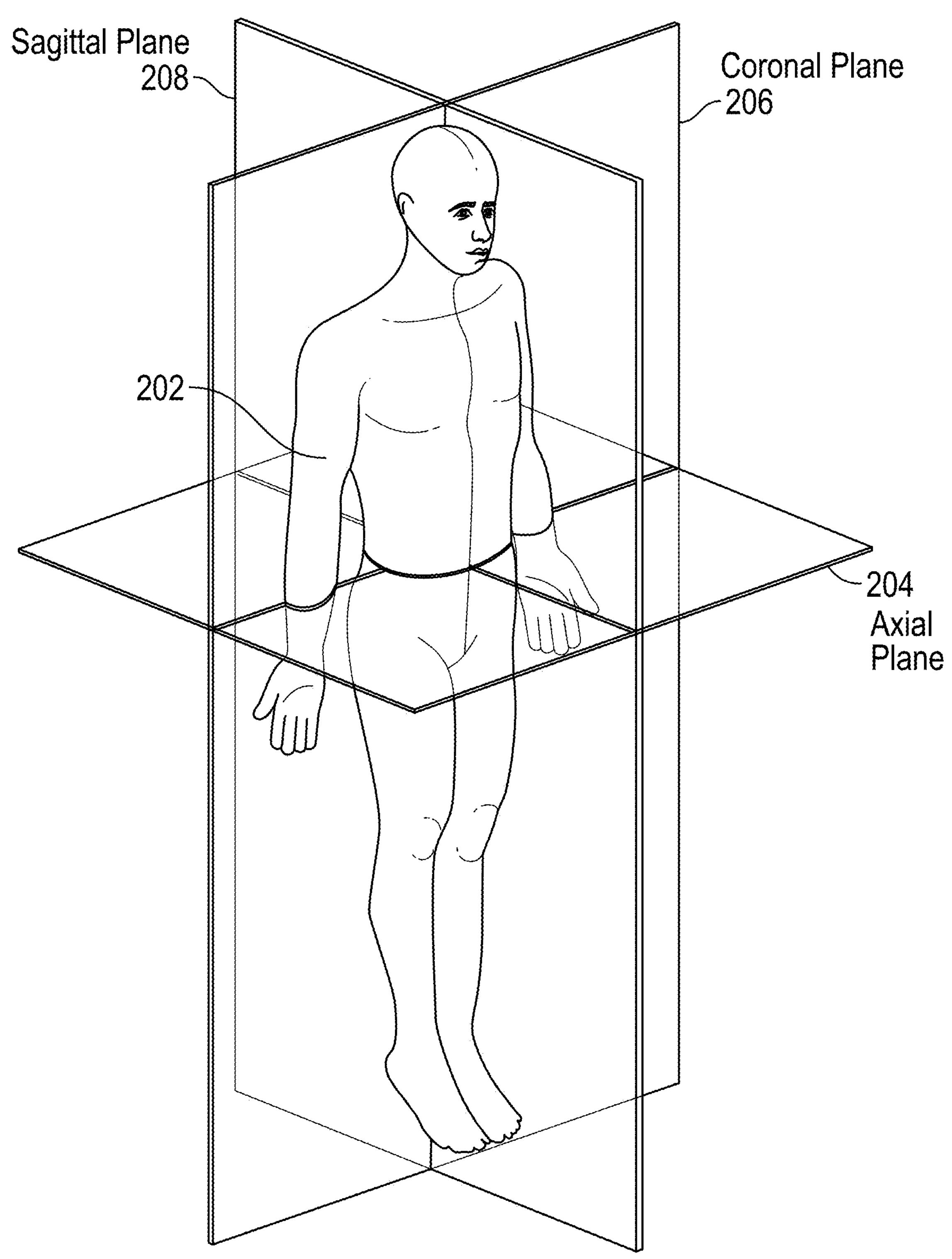
FIG. 2 illustrates an example of planes through a human being.

FIG. 2 illustrates an example of planes through a human being 202. As illustrated, the axial plane 204 (also known as the transverse plane, horizontal plane, or transaxial plane) is an anatomical plane that divides the body into superior (portions above) and inferior (portions below) sections. The coronal plane 206 divides the body into dorsal (of, on, or related to the upper side or back side of an animal) and ventral (of, on, or related to the underside or front of an animal) sections. The coronal plane 206 is perpendicular to the sagittal plane 208 (described below) and the axial plane 204. The sagittal plane 208 is a vertical plane which passes through the body 202 longitudinally. The sagittal plane 208 divides the body 202 into a left section and a right section.

Figure 3:
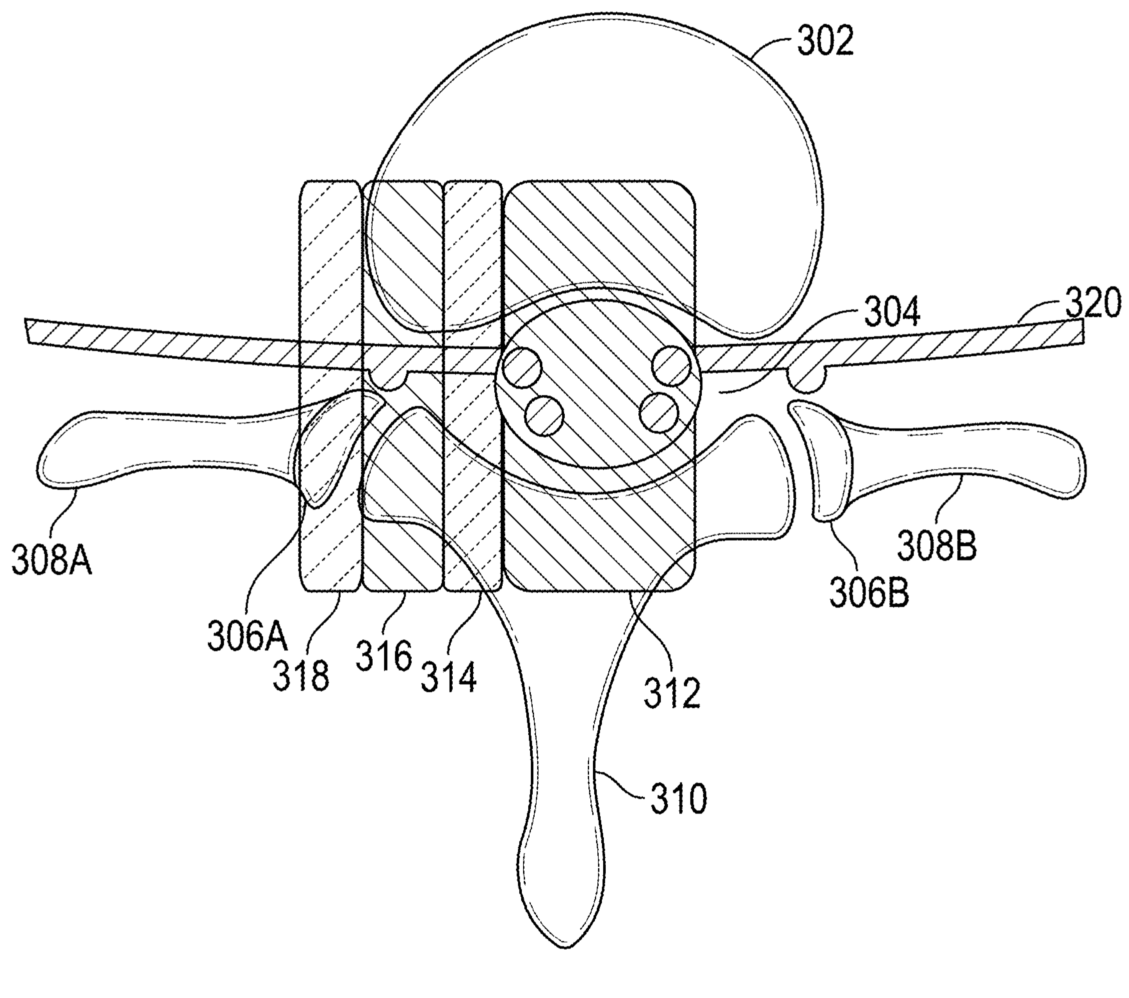
FIG. 3 illustrates a first example of a cross sectional view of a human vertebrae, spinal canal, and spinous process horizontally segmented.

FIG. 3 illustrates a first example of a superior view of a human vertebra 302, spinal canal 304, and spinous process 310 horizontally segmented within an axial plane. Other points of anatomy include the transverse process 308A, 308B, and the facet of superior articular process 306A, 306B, and a nerve root 320. The segments 312, 314, 316, 318 are horizontally segmented within the axial plane because, for a standing patient, the segments 312, 314, 316, 318 would form planar regions extending horizontally from the spinal canal. While in this example there are four segments 312, 314, 316, 318, in practice there would be, at the illustrated axial plane, at least seven segments, i.e., the central segment 312 (focused on the spinal canal 304), and three additional segments on each side. However, in practice, the number, size, and location of segments can vary according to anatomy. Various horizontal segments can be created, with each segment providing an area that can be used in subsequent volume calculations. For example, one segment 312 can have a width of the spinal canal 304. Another segment 314 can extend from the lateral edge of the spinal canal 304 a predefined width towards the transverse process 308A. Another segment 316 can continue from the edge of the previous segment 314 towards the edge of the spinous process 310, and a final segment 318 can continue from the edge of the spinous process 310 towards the transverse process 308A. In other configurations, the number or amount of segments and their precise locations can vary. In addition, while the segments illustrated in FIG. 3 are only on and extending to the left side of the spinal canal 304, in other configurations there can be additional segments on the right side of the spinal canal 304, or on both sides of the spinal canal 304. In addition, while the illustrated segments 312, 314, 316, 318 can extend laterally on both sides of the spinal canal 304, in other configurations, the segments 312, 314, 316, 318 can extend vertically (e.g., rectangular areas extending left-to-right in the illustration, with additional segments on top/below one another), have shapes other than rectangles (e.g., triangles, hexagons, etc.), or be otherwise arranged.

Figures 4, 5:
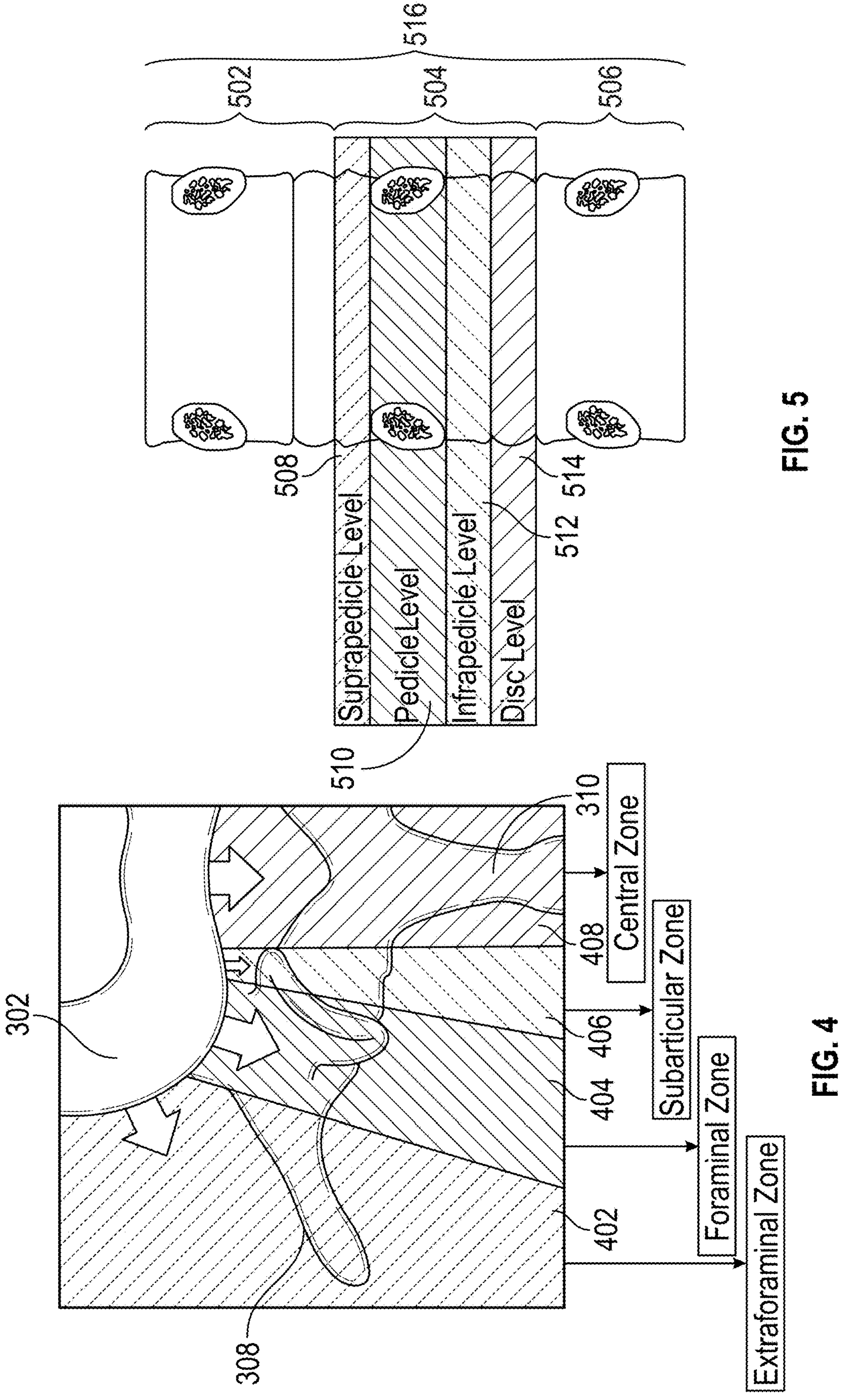
FIG. 4 illustrates a second example of a cross sectional view of a human vertebrae, spinal canal, and spinous process horizontally segmented in multiple planes.
FIG. 5 illustrates a third example of a cross sectional view of the spinal column and disks vertically segmented.

FIG. 4 illustrates a second example of a superior view of a human vertebrae 302, spinal canal, transverse process 308, and spinous process 310 horizontally segmented, with the segments 402, 404, 406, 408 being in an alternative, non-rectangular form compared to the segments 312, 314, 316, 318 illustrated in FIG. 3. In this example, the segments can be labeled as an Extraforaminal zone 402, a foraminal zone 404, a subarticular zone 406, and a central zone 408. As described with respect to FIG. 3, the segment shapes illustrated in FIG. 4 can vary according to configuration and need.

FIG. 5 illustrates an example of spinal column disks vertically segmented. In this example, multiple vertebrae 502, 504, 506 are illustrated, and a specific subsection 504 of those vertebrae is being segmented into vertical segments (also called level segments). The result is a disc level 514, an infrapedicle level 512, a pedicle level 510, and a suprapedicle level 508. These segments or levels 508, 510, 512, 514 can be used by the system to calculate volumes.

For example, the system can multiply the area of the pedicle level 510 by the area of the central zone 408 of FIG. 4. The resulting volume can then be used as a data point for the AI in predicting post-procedure volume. Other volumes are likewise possible, such that with the four segments 402, 404, 406, 408 of FIG. 4, and the four vertical segments or levels 508, 510, 512, 514, a total of sixteen volumes can be calculated based on the illustrated segments. Again, in other configurations, the number of such areas can increase or decrease as needed.

Figure 6:
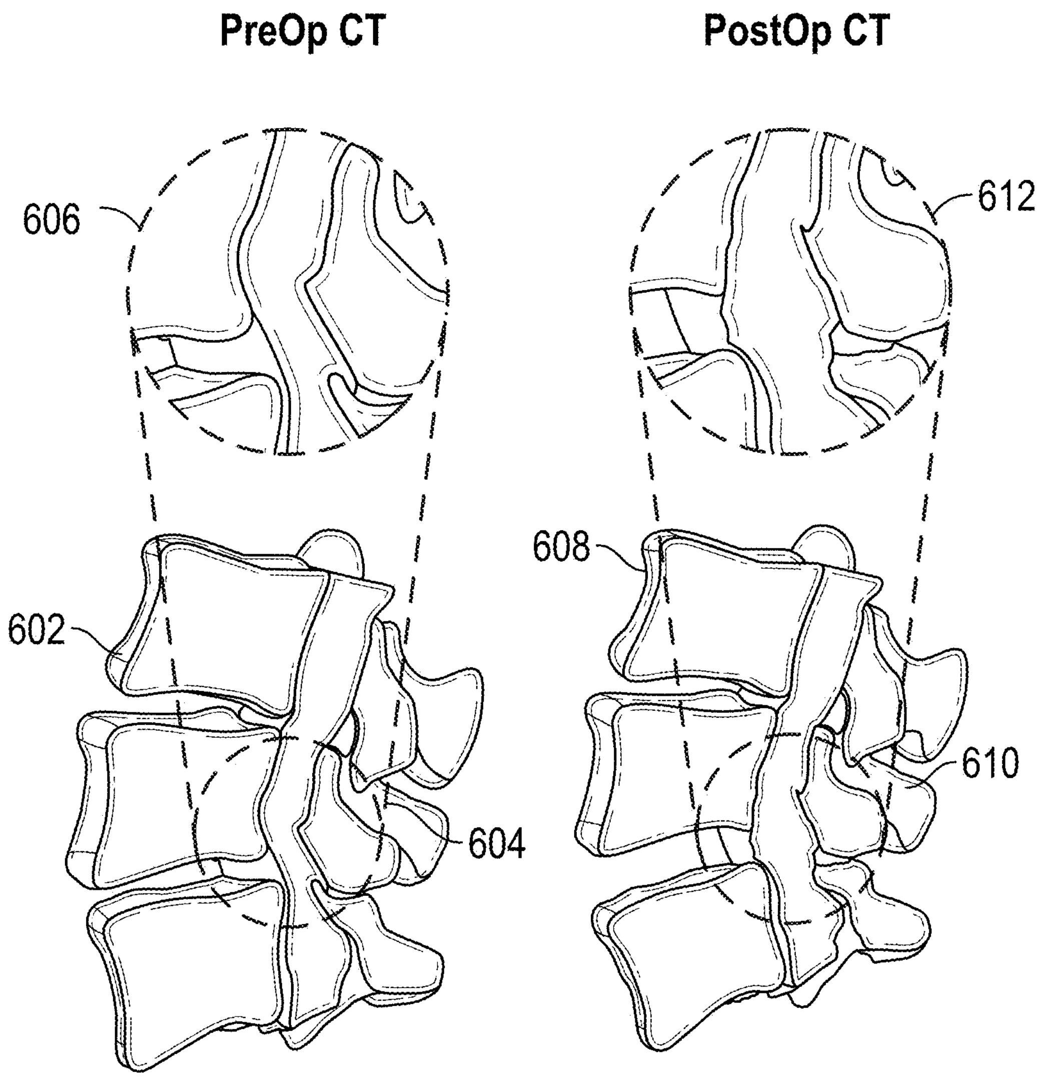
FIG. 6 illustrates an example of a spinal canal before and after a procedure.

FIG. 6 illustrates an example of a spinal canal before and after a procedure. In this example, a spine 602, 608 is captured via a pre-op CT image and a post-op CT image. In the pre-op CT image, a specific portion 604 of the spine 602 is circled, with a relatively higher amount of stenosis in that portion, as illustrated by the magnified/zoomed-in illustration of that portion 606. In the post-op CT image, that same portion 610 of the spine 608 is captured again, with the magnified/zoomed-in portion 612 illustrating that the stenosis has been reduced. Such pre- and post-op images can be used by the system to make predictions regarding future procedures, and can be used to further refine AI algorithms.

FIG. 7 illustrates an example method embodiment. As illustrated, the method can include: receiving, at a computer system, at least two pre-operation medical images, the at least two pre-operation medical images each capturing at least one functional spinal unit (702) and calculating, via at least one processor of the computer system using the at least two pre-operation medical images, an initial spinal canal regional volume for at least a portion of the at least one functional spinal unit (704). The method can then include identifying a plurality of spine surgery options (706) and calculating, via the at least one processor executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options (708). The method can then conclude with selecting, based at least in part on the plurality of predicted spinal canal regional volumes, a selected spine surgery option from the plurality of spine surgery options, such that the selected spine surgery option is executed on the at least one functional spinal unit (710).

In some configurations, the at least two pre-operation medical images are part of a pre-operation medical study, where a number of images of an individual (e.g., a patient) are taken. Such images can be in any format (e.g., CT, MRI, X-ray, sonogram, etc.). These images can, for example, include or be reformatted to include multiple axial images, multiple sagittal images, and/or multiple coronal images, such that a single study can contain images from multiple planes (see, e.g., FIG. 2).

In some configurations, the illustrated method of FIG. 7 can further include: receiving, at the computer system after execution of the selected spine surgery option, at least two post-operation medical images, the at least two post-operation medical images capturing the at least one functional spinal unit; calculating, via the at least one processor of the computer system using the at least two post-operation medical images, a post-operation spinal canal regional volume; comparing, via the at least one processor, the post-operation spinal canal regional volume to the initial spinal canal regional volume, resulting in a comparison; and updating the neural network based on the comparison. In such configurations, the comparing can further include comparing the post-operation spinal canal regional volume to at least one predicted spinal canal regional volume of the plurality of predicted spinal canal regional volumes, wherein one predicted spinal canal regional volume within the at least one predicted spinal canal regional volume is based on the selected spine surgery option.

In some configurations, the neural network further predicts, for each of the plurality of spine surgery options, a predicted stenosis resolution, resulting in a plurality of predicted stenosis resolutions; and wherein the selected spine surgery option is selected, at least in part, based on which of the plurality of spine surgery options is most likely to reduce stenosis symptoms.

In some configurations, each pre-operation medical image in the at least two pre-operation medical images is at least one of a CT, a MRI, an X-ray and an Ultrasound image.

In some configurations, the illustrated method of FIG. 7 can further include: generating regional volumetric stenosis measurements of the at least one functional spinal unit, wherein the calculating of the initial spinal canal regional volume is further based on the regional volumetric stenosis measurements; and wherein the neural network receives the regional volumetric stenosis measurements as inputs. In such configurations, the regional volumetric stenosis measurements can include: canal regions comprising: central, lateral recess, and foraminal; and level regions comprising: disc level, vertebral body level, and pedicle level.

In another aspect of the invention, the automated volumetric spinal stenosis assessment can include one or more of the following.

In another aspect, the spinal stenosis is the pathological process where the spinal canal narrows due to the age-related degenerative changes thereby compressing the nerves in the canal obstructing the signal flow to and from the brain to the lower extremities resulting in pain heaviness and weakness in the legs when walking. In accordance with the principles of the invention, an automated method is provided to measure the extent of the stenosis. This is a beneficial advantage over relying on manual measurements of CT scan and MRI scan images that are area measurements which can be misleading. The automated volumetric spinal stenosis feature in accordance with the principles of the invention will harness the volumetric segmentation capabilities of the automated segmentation module to produce automated regional volumetric stenosis measurements (central, lateral recess, foraminal and subarticular).

1) A method to define the canal regions i) central ii) lateral recess/subarticular and iii) foraminal, at the three levels 1) disc level 2) vertebral body level and the 3) pedicle level.
2) A method to measure the canal regions.
3) A method to inform the surgeon as a tool to plan the extent of surgery.
4) A method to predict the outcome of surgery using volume data.
5) A method to correlate the extent of decompression with clinical outcome.
6) A method to evaluate the extent of decompression achieved by the surgeon.

For example, for a central epidural volume at disc space level, the system may do a pre-op to post-op comparison such as that illustrated in Table 1 below, with the result showing the percentage of relative change:

TABLE 1

| | Pre-Op Volume (cc) | Post-Op Volume (cc) | % Relative Change |
|---|---|---|---|
| L3 Disc Level | 2.01699 | 3.35882 | 66.53% |
| L4 Disc Level | 0.292988 | 1.28023 | 336.96% |
| L5 Disc Level | 0.346762 | 2.06294 | 494.92% |

FIG. 8 illustrates an example method embodiment. As illustrated, the method can include: receiving, at a computer system, at least two pre-operation medical images, the at least two pre-operation medical images each capturing at least one functional spinal unit (802) and calculating, via at least one processor of the computer system using the at least two pre-operation medical images, an initial spinal canal regional volume for at least a portion of the at least one functional spinal unit (804). The method can then include identifying a plurality of spine surgery options (806) and calculating, via the at least one processor executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options (808). The method can then include with selecting, based at least in part on the plurality of predicted spinal canal regional volumes, a selected spine surgery option from the plurality of spine surgery options, such that the selected spine surgery option is executed on the at least one functional spinal unit (810). The method can than include receiving, after executing the selected spine surgery option, at least two post-operation medical images, the at least two post-operation medical images capturing the at least one functional spinal unit (812) and updating the neural network based at least in part on the at least two post-operation medical images (814).

Figure 9:
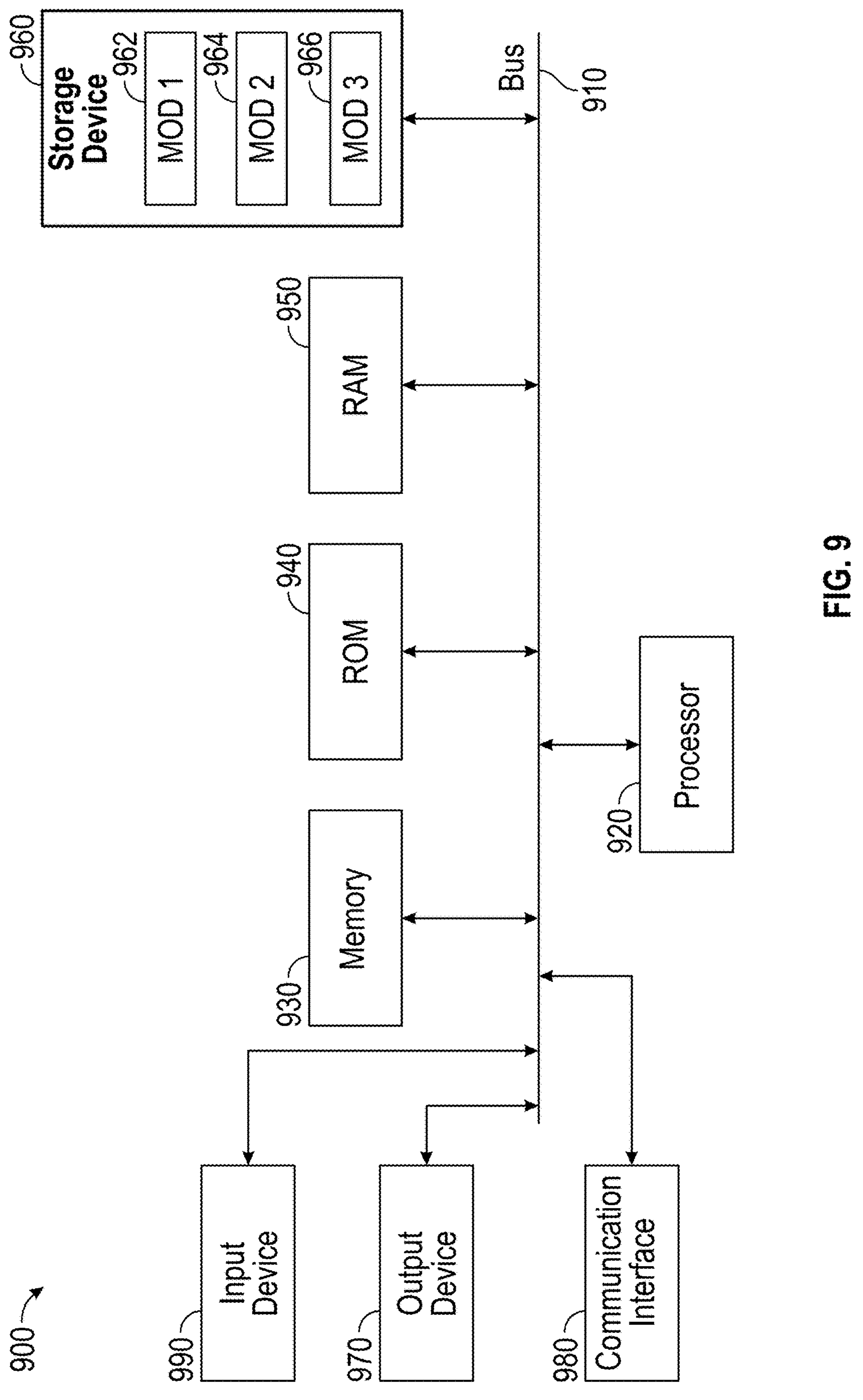
FIG. 9 illustrates an example computer system.

With reference to FIG. 9, an exemplary system includes a computing device 900 (such as a general-purpose computing device), including a processing unit (CPU or processor) 920 and a system bus 910 that couples various system components including the system memory 930 such as read-only memory (ROM) 940 and random access memory (RAM) 950 to the processor 920. The computing device 900 can include a cache of high-speed memory connected directly with, in close proximity to, or integrated as part of the processor 920. The computing device 900 copies data from the system memory 930 and/or a storage device 960 to the cache for quick access by the processor 920. In this way, the cache provides a performance boost that avoids processor 920 delays while waiting for data. These and other modules can control or be configured to control the processor 920 to perform various actions. Other system memory 930 may be available for use as well. The system memory 930 can include multiple different types of memory with different performance characteristics. It can be appreciated that the disclosure may operate on a computing device 900 with more than one processor 920 or on a group or cluster of computing devices networked together to provide greater processing capability. The processor 920 can include any general-purpose processor and a hardware module or software module, such as module 1 (MOD 1) 962, module 2 (MOD 2) 964, and module 3 (MOD 3) 966 stored in storage device 960, configured to control the processor 920 as well as a special-purpose processor where software instructions are incorporated into the actual processor design. The processor 920 may essentially be a completely self-contained computing system, containing multiple cores or processors, a bus, memory controller, cache, etc. A multi-core processor may be symmetric or asymmetric.

The system bus 910 may be any of several types of bus structures including a memory bus or memory controller, a peripheral bus, and a local bus using any of a variety of bus architectures. A basic input/output (BIOS) stored in read-only memory (ROM) 940 or the like, may provide the basic routine that helps to transfer information between elements within the computing device 900, such as during start-up. The computing device 900 further includes a storage device(s) 960 such as a hard disk drive, a magnetic disk drive, an optical disk drive, tape drive or the like. The storage device 960 can include software modules 962, 964, 966 for controlling the processor 920. Other hardware or software modules are contemplated. The storage device 960 is connected to the system bus 910 by a drive interface. The drives and the associated computer-readable storage media provide nonvolatile storage of computer-readable instructions, data structures, program modules and other data for the computing device 900. In one aspect, a hardware module that performs a particular function includes the software component stored in a tangible computer-readable storage medium in connection with the necessary hardware components, such as the processor 920, system bus 910, output device 970 (such as a display or speaker), and so forth, to carry out the function. In another aspect, the system can use a processor and computer-readable storage medium to store instructions which, when executed by a processor (e.g., one or more processors), cause the processor to perform a method or other specific actions. The basic components and appropriate variations are contemplated depending on the type of device, such as whether the computing device 900 is a small, handheld computing device, a desktop computer, or a computer server.

Although the exemplary embodiment described herein employs the storage device 960 (such as a hard disk), other types of computer-readable media which can store data that are accessible by a computer, such as magnetic cassettes, flash memory cards, digital versatile disks, cartridges, random access memories (RAMs) 950, and read-only memory (ROM) 940, may also be used in the exemplary operating environment. Tangible computer-readable storage media, computer-readable storage devices, or computer-readable memory devices, expressly exclude media such as transitory waves, energy, carrier signals, electromagnetic waves, and signals per sc.

To enable user interaction with the computing device 900, an input device 990 represents any number of input mechanisms, such as a microphone for speech, a touch-sensitive screen for gesture or graphical input, keyboard, mouse, motion input, speech and so forth. An output device 970 can also be one or more of a number of output mechanisms known to those of skill in the art. In some instances, multimodal systems enable a user to provide multiple types of input to communicate with the computing device 900. The communications interface 980 generally governs and manages the user input and system output. There is no restriction on operating on any particular hardware arrangement and therefore the basic features here may easily be substituted for improved hardware or firmware arrangements as they are developed.

The technology discussed herein refers to computer-based systems and actions taken by, and information sent to and from, computer-based systems. One of ordinary skill in the art will recognize that the inherent flexibility of computer-based systems allows for a great variety of possible configurations, combinations, and divisions of tasks and functionality between and among components. For instance, processes discussed herein can be implemented using a single computing device or multiple computing devices working in combination. Databases, memory, instructions, and applications can be implemented on a single system or distributed across multiple systems. Distributed components can operate sequentially or in parallel.

Use of language such as "at least one of X, Y, and Z," "at least one of X, Y, or Z," "at least one or more of X, Y, and Z," "at least one or more of X, Y, or Z," "at least one or more of X, Y, and/or Z," or "at least one of X, Y, and/or Z," are intended to be inclusive of both a single item (e.g., just X, or just Y, or just Z) and multiple items (e.g., {X and Y}, {X and Z}, {Y and Z}, or {X, Y, and Z}). The phrase "at least one of" and similar phrases are not intended to convey a requirement that each possible item must be present, although each possible item may be present.

The various embodiments described above are provided by way of illustration only and should not be construed to limit the scope of the disclosure. Various modifications and changes may be made to the principles described herein without following the example embodiments and applications illustrated and described herein, and without departing from the spirit and scope of the disclosure. For example, unless otherwise explicitly indicated, the steps of a process or method may be performed in an order other than the example embodiments discussed above. Likewise, unless otherwise indicated, various components may be omitted, substituted, or arranged in a configuration other than the example embodiments discussed above.

Further aspects of the present disclosure are provided by the subject matter of the following clauses.

A method comprising: receiving at least two pre-operation medical images, the at least two pre-operation medical images each capturing at least one functional spinal unit; calculating, using the at least two pre-operation medical images, an initial spinal canal regional volume for at least a portion of the at least one functional spinal unit; identifying a plurality of spine surgery options; calculating a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

A method comprising: receiving, at a computer system, at least two pre-operation medical images, the at least two pre-operation medical images each capturing at least one functional spinal unit; calculating, via at least one processor of the computer system using the at least two pre-operation medical images, an initial spinal canal regional volume for at least a portion of the at least one functional spinal unit; identifying a plurality of spine surgery options; calculating, via the at least one processor executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

The method of any preceding clause, wherein the at least two pre-operation medical images are part of a pre-operation medical study.

The method of any preceding clause, further comprising: receiving, at the computer system after execution of the selected spine surgery option, at least two post-operation medical images, the at least two post-operation medical images capturing the at least one functional spinal unit; calculating, via the at least one processor of the computer system using the at least two post-operation medical images, a post-operation spinal canal regional volume; comparing, via the at least one processor, the post-operation spinal canal regional volume to the initial spinal canal regional volume, resulting in a comparison; and updating the neural network based on the comparison.

The method of any preceding clause, wherein the comparing further comprises comparing the post-operation spinal canal regional volume to at least one predicted spinal canal regional volume of the plurality of predicted spinal canal regional volumes, wherein one predicted spinal canal regional volume within the at least one predicted spinal canal regional volume is based on the selected spine surgery option.

The method of any preceding clause, wherein the neural network further predicts, for each of the plurality of spine surgery options, a predicted stenosis resolution, resulting in a plurality of predicted stenosis resolutions; and wherein the selected spine surgery option is selected, at least in part, based on which of the plurality of spine surgery options is most likely to reduce stenosis symptoms.

The method of any preceding clause, wherein each pre-operation medical image in the at least two pre-operation medical images is at least one of a CT, a MRI, an X-ray and an Ultrasound image.

The method of any preceding clause, further comprising: generating regional volumetric stenosis measurements of the at least one functional spinal unit, wherein the calculating of the initial spinal canal regional volume is further based on the regional volumetric stenosis measurements; and wherein the neural network receives the regional volumetric stenosis measurements as inputs.

The method of any preceding clause, wherein the regional volumetric stenosis measurements comprise: canal regions comprising: central, lateral recess, and foraminal; and level regions comprising: disc level, vertebral body level, and pedicle level.

A system comprising: at least one processor; and a non-transitory computer-readable storage medium having instructions stored which, when executed by the at least one processor, cause the at least one processor to perform operations comprising: receiving at least two pre-operation medical images, the at least two pre-operation medical images each capturing at least one functional spinal unit; calculating, using the at least two pre-operation medical images, an initial spinal canal regional volume for at least a portion of the at least one functional spinal unit; identifying a plurality of spine surgery options; calculating, by executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

The system of any preceding clause, wherein the at least two pre-operation medical images are part of a pre-operation medical study.

The system of any preceding clause, the non-transitory computer-readable storage medium having additional instructions stored which, when executed by the at least one processor, cause the at least one processor to perform operations comprising: receiving, after execution of the selected spine surgery option, at least two post-operation medical images, the at least two post-operation medical images capturing the at least one functional spinal unit; calculating, using the at least two post-operation medical images, a post-operation spinal canal regional volume; comparing the post-operation spinal canal regional volume to the initial spinal canal regional volume, resulting in a comparison; and updating the neural network based on the comparison.

The system of any preceding clause, wherein the comparing further comprises comparing the post-operation spinal canal regional volume to at least one predicted spinal canal regional volume of the plurality of predicted spinal canal regional volumes, wherein one predicted spinal canal regional volume within the at least one predicted spinal canal regional volume is based on the selected spine surgery option.

The system of any preceding clause, wherein the neural network further predicts, for each of the plurality of spine surgery options, a predicted stenosis resolution, resulting in a plurality of predicted stenosis resolutions; and wherein the selected spine surgery option is selected, at least in part, based on which of the plurality of spine surgery options is most likely to reduce stenosis symptoms.

The system of any preceding clause, wherein each pre-operation medical image in the at least two pre-operation medical images is at least one of a CT, a MRI, an X-ray and an Ultrasound image.

The system of any preceding clause, the non-transitory computer-readable storage medium having additional instructions stored which, when executed by the at least one processor, cause the at least one processor to perform operations comprising: generating regional volumetric stenosis measurements of the at least one functional spinal unit, wherein the calculating of the initial spinal canal regional volume is further based on the regional volumetric stenosis measurements; and wherein the neural network receives the regional volumetric stenosis measurements as inputs.

The system of any preceding clause, wherein the regional volumetric stenosis measurements comprise: canal regions comprising: central, lateral recess, and foraminal; and level regions comprising: disc level, vertebral body level, and pedicle level.

A non-transitory computer-readable storage medium having instructions stored which, when executed by at least one processor, cause the at least one processor to perform operations comprising: receiving at least two pre-operation medical images, the at least two pre-operation medical images each capturing at least one functional spinal unit; calculating, using the at least two pre-operation medical images, an initial spinal canal regional volume for at least a portion of the at least one functional spinal unit; identifying a plurality of spine surgery options; calculating, by executing a neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

The non-transitory computer-readable storage medium of any preceding clause, wherein the at least two pre-operation medical images are part of a pre-operation medical study.

The non-transitory computer-readable storage medium of any preceding clause, having additional instructions stored which, when executed by the at least one processor, cause the at least one processor to perform operations comprising: receiving, after execution of the selected spine surgery option, at least two post-operation medical images, the at least two post-operation medical images capturing the at least one functional spinal unit; calculating, using the at least two post-operation medical images, a post-operation spinal canal regional volume; comparing the post-operation spinal canal regional volume to the initial spinal canal regional volume, resulting in a comparison; and updating the neural network based on the comparison.

The non-transitory computer-readable storage medium of any preceding clause, wherein the comparing further comprises comparing the post-operation spinal canal regional volume to at least one predicted spinal canal regional volume of the plurality of predicted spinal canal regional volumes, wherein one predicted spinal canal regional volume within the at least one predicted spinal canal regional volume is based on the selected spine surgery option.

We claim:

1. A method comprising:

receiving, at a computer system, at least two pre-operation medical images, the at least two pre-operation medical images each capturing at least one functional spinal unit;

generating regional volumetric stenosis measurements of the at least one functional spinal unit;

calculating, via at least one processor of the computer system using the at least two pre-operation medical images and the regional volumetric stenosis measurements, an initial spinal canal regional volume for at least a portion of the at least one functional spinal unit;

identifying a plurality of spine surgery options;

calculating, via the at least one processor executing a neural network wherein the regional volumetric stenosis measurements are inputs to the neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

2. The method of claim 1, wherein the at least two pre-operation medical images are part of a pre-operation medical study.

3. The method of claim 1, further comprising:

receiving, at the computer system after execution of the selected spine surgery option, at least two post-operation medical images, the at least two post-operation medical images capturing the at least one functional spinal unit;

calculating, via the at least one processor of the computer system using the at least two post-operation medical images, a post-operation spinal canal regional volume;

comparing, via the at least one processor, the post-operation spinal canal regional volume to the initial spinal canal regional volume, resulting in a comparison; and updating the neural network based on the comparison.

4. The method of claim 3, wherein the comparing further comprises comparing the post-operation spinal canal regional volume to at least one predicted spinal canal regional volume of the plurality of predicted spinal canal regional volumes, wherein one predicted spinal canal regional volume within the at least one predicted spinal canal regional volume is based on the selected spine surgery option.

5. The method of claim 1, wherein the neural network further predicts, for each of the plurality of spine surgery options, a predicted stenosis resolution, resulting in a plurality of predicted stenosis resolutions; and wherein the selected spine surgery option is selected, at least in part, based on which of the plurality of spine surgery options is most likely to reduce stenosis symptoms.

6. The method of claim 1, wherein each pre-operation medical image in the at least two pre-operation medical images is at least one of a CT, a MRI, an X-ray and an Ultrasound image.

7. The method of claim 1, wherein the regional volumetric stenosis measurements comprise:

canal regions comprising: central, lateral recess, and foraminal; and level regions comprising: disc level, vertebral body level, and pedicle level.

8. A system comprising:

at least one processor; and a non-transitory computer-readable storage medium having instructions stored which, when executed by the at least one processor, cause the at least one processor to perform operations comprising:

receiving at least two pre-operation medical images, the at least two pre-operation medical images each capturing at least one functional spinal unit;

generating regional volumetric stenosis measurements of the at least one functional spinal unit;

calculating, using the at least two pre-operation medical images and the regional volumetric stenosis measurements, an initial spinal canal regional volume for at least a portion of the at least one functional spinal unit;

identifying a plurality of spine surgery options;

calculating, by executing a neural network wherein the regional volumetric stenosis measurements are inputs to the neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

9. The system of claim 8, wherein the at least two pre-operation medical images are part of a pre-operation medical study.

10. The system of claim 8, the non-transitory computer-readable storage medium having additional instructions stored which, when executed by the at least one processor, cause the at least one processor to perform operations comprising:

receiving, after execution of the selected spine surgery option, at least two post-operation medical images, the at least two post-operation medical images capturing the at least one functional spinal unit;

calculating, using the at least two post-operation medical images, a post-operation spinal canal regional volume;

comparing the post-operation spinal canal regional volume to the initial spinal canal regional volume, resulting in a comparison; and updating the neural network based on the comparison.

11. The system of claim 10, wherein the comparing further comprises comparing the post-operation spinal canal regional volume to at least one predicted spinal canal regional volume of the plurality of predicted spinal canal regional volumes, wherein one predicted spinal canal regional volume within the at least one predicted spinal canal regional volume is based on the selected spine surgery option.

12. The system of claim 8, wherein the neural network further predicts, for each of the plurality of spine surgery options, a predicted stenosis resolution, resulting in a plurality of predicted stenosis resolutions; and wherein the selected spine surgery option is selected, at least in part, based on which of the plurality of spine surgery options is most likely to reduce stenosis symptoms.

13. The system of claim 8, wherein each pre-operation medical image in the at least two pre-operation medical images is at least one of a CT, a MRI, an X-ray and an Ultrasound image.

14. The system of claim 8, wherein the regional volumetric stenosis measurements comprise:

canal regions comprising: central, lateral recess, and foraminal; and level regions comprising: disc level, vertebral body level, and pedicle level.

15. A non-transitory computer-readable storage medium having instructions stored which, when executed by at least one processor, cause the at least one processor to perform operations comprising:

receiving at least two pre-operation medical images, the at least two pre-operation medical images each capturing at least one functional spinal unit;

generating regional volumetric stenosis measurements of the at least one functional spinal unit;

calculating, using the at least two pre-operation medical images and the regional volumetric stenosis measurements, an initial spinal canal regional volume for at least a portion of the at least one functional spinal unit;

identifying a plurality of spine surgery options;

calculating, by executing a neural network wherein the regional volumetric stenosis measurements are inputs to the neural network, a predicted spinal canal regional volume for the at least a portion of the at least one functional spinal unit undergoing each of the plurality of spine surgery options separately, resulting in a plurality of predicted spinal canal regional volumes corresponding to the plurality of spine surgery options; and selecting, based at least in part on the plurality of predicted spinal canal regional volumes, a selected spine surgery option from the plurality of spine surgery options, such that the selected spine surgery option is executed on the at least one functional spinal unit.

16. The non-transitory computer-readable storage medium of claim 15, wherein the at least two pre-operation medical images are part of a pre-operation medical study.

17. The non-transitory computer-readable storage medium of claim 15, having additional instructions stored which, when executed by the at least one processor, cause the at least one processor to perform operations comprising:

receiving, after execution of the selected spine surgery option, at least two post-operation medical images, the at least two post-operation medical images capturing the at least one functional spinal unit;

calculating, using the at least two post-operation medical images, a post-operation spinal canal regional volume;

comparing the post-operation spinal canal regional volume to the initial spinal canal regional volume, resulting in a comparison; and updating the neural network based on the comparison.

18. The non-transitory computer-readable storage medium of claim 17, wherein the comparing further comprises comparing the post-operation spinal canal regional volume to at least one predicted spinal canal regional volume of the plurality of predicted spinal canal regional volumes, wherein one predicted spinal canal regional volume within the at least one predicted spinal canal regional volume is based on the selected spine surgery option.

* * * * *